Figure 1:
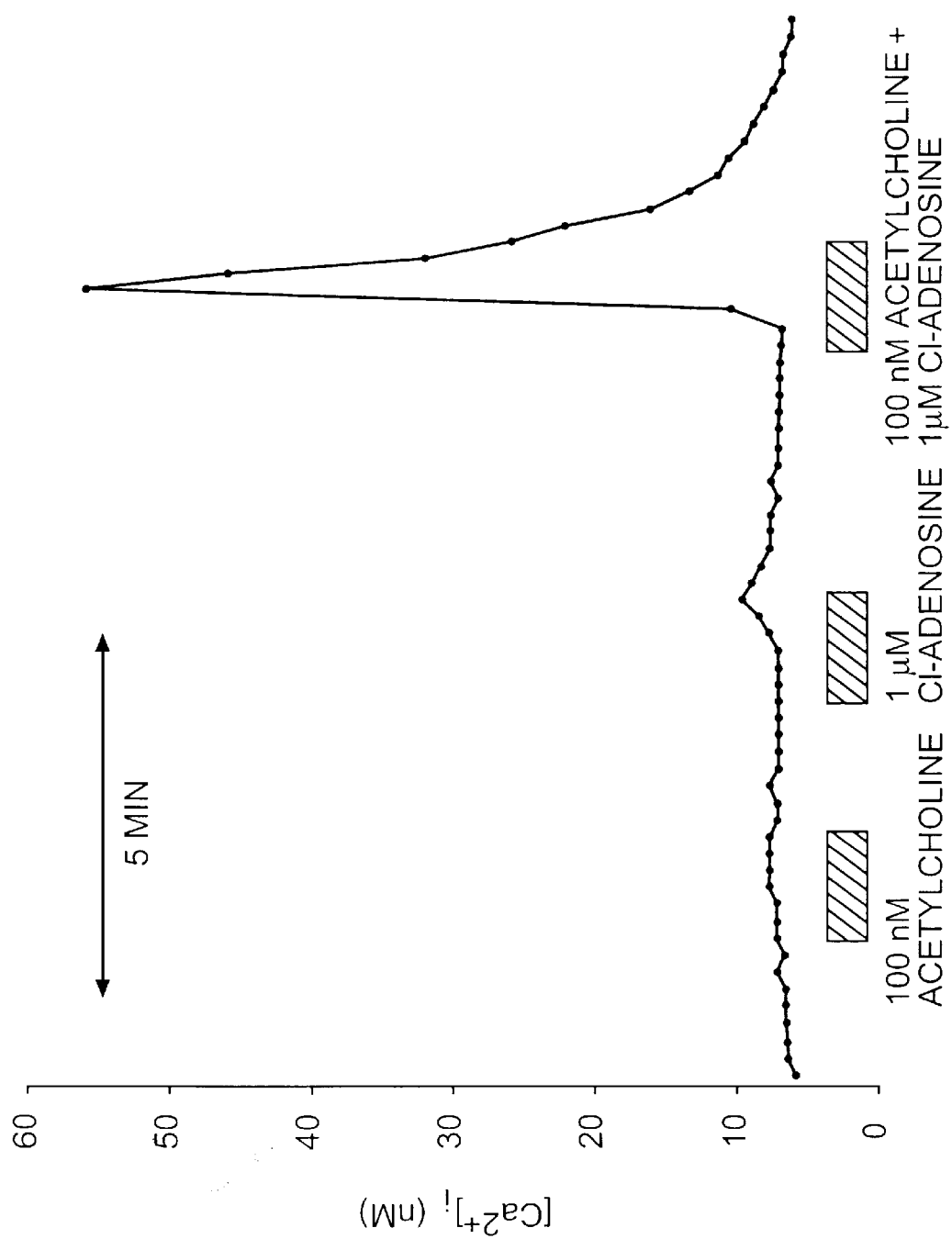

United States Patent [19]
Schubert et al.

[11] Patent Number: 6,037,347
[45] Date of Patent: Mar. 14, 2000

[54] COMBINATION PREPARATION FOR USE IN DEMENTIA

[75] Inventors: Hans-Peter Schubert, Apfeldorf; Hildegard Nimmesgern, Darmstadt; Karl Rudolphi, Mainz, all of Germany

[73] Assignee: Hoechst Aktiengesellschaft, Frankfurt am Main, Germany

[21] Appl. No.: 09/030,207

[22] Filed: Feb. 25, 1998

[30] Foreign Application Priority Data

Feb. 26, 1997 [DE] Germany ............................ 197 07 655

[51] Int. Cl.⁷ ........................ A61K 31/52; A61K 31/445; C09B 219/00; C07D 473/08; C07D 211/00

[52] U.S. Cl. .......................... 514/264; 514/263; 514/297; 514/315; 546/104; 544/267

[58] Field of Search ..................................... 514/264, 263, 514/297, 315; 546/11, 104; 544/267; 424/472

[56] References Cited

U.S. PATENT DOCUMENTS

| | | | |
|---|---|---|---|
| 3,621,096 | 11/1971 | Prange, Jr. et al. | 514/217 |
| 3,737,433 | 6/1973 | Mohler et al. | 544/271 |
| 4,273,774 | 6/1981 | Scherm | 514/264 |
| 4,289,776 | 9/1981 | Mohler et al. | 424/253 |
| 4,719,212 | 1/1988 | Goto et al. | 514/263 |
| 4,833,146 | 5/1989 | Gebert et al. | 514/263 |
| 5,118,500 | 6/1992 | Hanel et al. | 424/85.1 |
| 5,783,584 | 7/1998 | Pang et al. | 514/297 |
| 5,837,724 | 11/1998 | Allen et al. | 514/422 |

OTHER PUBLICATIONS

Wallis, R.M., Napier C.M., "Muscarinic Antagonists in development for disorders of smooth muscle function," *Life–Sci.*, 64 (6–7), pp. 395–401. Abstract only. (1999).

Choppin, A., Eglen, R.M., Hegde, S.S., "Pharmacological characterization of muscarinic receptors in rabbit isolated iris sphincter muscle and urinary bladder smooth muscle," *Br. J. Pharmacol.*, vol. 124, pp. 883–888. Jul. 1998. Abstract only.

Gillberg, P.G., Sundquist, S., Nilvebrant, L., "Comparison of the in vitro profiles of tolterodine with those of subtype–selective muscarinic receptor antagonists," *Eur. J. Pharmacol.* (May 1998) vol. 349, pp. 285–292.

Beaumont, K.C., Cussans, N.J., Nichols, D.J., Smith, D.A., "Pharmacokinetics and metabolism of darifenacin in the mouse, rat, dog and man," *Xenobiotica*, 28 (1), pp. 63–75. Abstract only. (Jan. 1998).

Hegde, S.S., Choppin, A., Bonhaus, D., Briaud, S., Loeb, M., Moy, T.M., Loury, D., Eglen, R.M., "Functional role of M2 and M3 muscarinic receptors in the urinary bladder of rats in vitro and in vivo," *Br. J. Pharmacol.*, vol. 120 (8), pp. 1409–18. Abstract only. (Apr. 1997).

Smith, C.M., Wallis, R.M., "Characterisation of [3H]–darifenacin as a novel radioligand for the study of muscarinic M3 receptors," *J. Recpt. Signal–Transduct–Res.*, 17 (1–3), pp. 177–84. (May 1997). Abstract only.

Alabaster, V.A., "Discovery & development of selective M3 antagonists for clinical use," *Life–Sci.*, 60, pp. 1053–60. Abstract only. (1997).

Kaye, B., Herron, W.J., P.V., Robinson, S., Stophe, D.A., Venn, R.F., Wild, W., "Rapid, solid phase extraction technique for the high–throughout assay of darifenacin in human plasma," *Anal.Chem.*, 68(9), pp. 1658–60. (May 1996) Abstract only.

H. Akiyama et al., "Morphological Diversities of CD44 Positive Astrocytes in The Cerebral Cortex of Normal Subjects and Patients with Alzheimer's Disease", Brain Research, 632:249–259 (1993).

H. Tohgi et al., "Remarkable Reduction in Acetylcholine Concentration in the Cerebrospinal Fluid From Patients With Alzheimer Type Dementia", Neuroscience Letters, 177:139–142 (1994).

J. Daly et al., "Adenosine Receptors in the Central Nervous System: Relationship to the Central Actions of Methylxanthines", Life Sciences, 28 (19) :2083–2097 (1981).

M. Ballarín et al., "Extracellular Levels of Adenosine and its Metabolites in the Striatum of Awake Rats: Inhibition of Uptake and Metabolism", Acta Physiol Scand, 142:97–103 (1991).

F. Parkinson et al., "Propentofylline: A Nuceloside Transport Inhibitor with Neuroprotective Effects in Cerebral Ischemia", Gen. Pharmac., 25 (6) :1053–1058 (1994).

E. Messamore et al., "Astrocytes Associated with Senile Plaques Possess Muscarinic Acetylcholine Receptors", NeuroReport, 5 (12) :1473–1476 (Jul. 1994).

Nitahara et al. Neuroscience, 67 (1), pp. 159–168. (Jul. 1995).

*Primary Examiner*—Ralph Gitomer
*Assistant Examiner*—Marjorie A. Moran
*Attorney, Agent, or Firm*—Finnegan, Henderson, Farabow, Garrett & Dunner, L.L.P.

[57] ABSTRACT

The invention relates to a composition which is a pharmaceutical combination preparation comprising a compound which has an acetylcholinesterase-inhibitory action or exhibits muscarinergic action and a compound which increases the endogenous extracellular adenosine level, wherein the combination preparation is suitable for the treatment of dementia. The invention further relates to a process for the production of the combination preparation. The invention additionally relates to a process for treating patients in need of suitable therapy with the combination preparation.

21 Claims, 3 Drawing Sheets

COMBINATION PREPARATION FOR USE IN DEMENTIA

The invention relates to a composition which is a pharmaceutical combination preparation for the treatment of dementia as a result of neurodegenerative disorders which accompany destruction of cholinergic neurons and cholinergic deficit (Tohgi et al., Neurosci. Lett. 177 (1994), pages 1939–1942). These combination preparations compensate for the cholinergic deficit by an increase in the $Ca^{2+}$-dependent signal transmission induced by means of muscarinic receptor stimulation. Such an increase can be achieved by cooperative adenosine actions, namely by a combination of substances which increase the extracellular adenosine concentration with muscarinic receptor agonists or acetylcholinesterase inhibitors ("AChE inhibitors").

The pharmacological strategy mainly followed until now for the therapy of senile dementia is the maintenance of muscarinic receptor activation by administration of muscarinergic agonists or of AChE inhibitors which increase the concentration of endogenous acetylcholine ("ACh") at the receptor. Whether, on continuing destruction of cholinergic neuron systems, an increase in the ACh level sufficient for proper cell function can actually be achieved by AChE inhibition, is questionable. Further, together with lack of specificity, AChE inhibitors exhibit considerable side effects. A potentiation of the action of insufficient ACh concentrations mediated via muscarinic receptors by other mechanisms would therefore be desirable and could be a basis for the development of an appropriate combination therapy.

It is known that ACh affects not only the functions of nerve cells, but also of glia cells (i.e., astrocytes) (Messamore et al., Neuroreport, 5, pages 1473–1476, (1994)). Since pathological glia cell reactions obviously play an important part in the pathophysiology of dementia (Akiyama et al., Brain Res. 632, pages 249–259, (1993)), cultured astrocytes were selected as an vitro model system. The effect on the intracellular $Ca^{2+}$ release induced by muscarinic receptors was investigated with the aid of the dynamic fluorescence imaging method.

Figure 2:
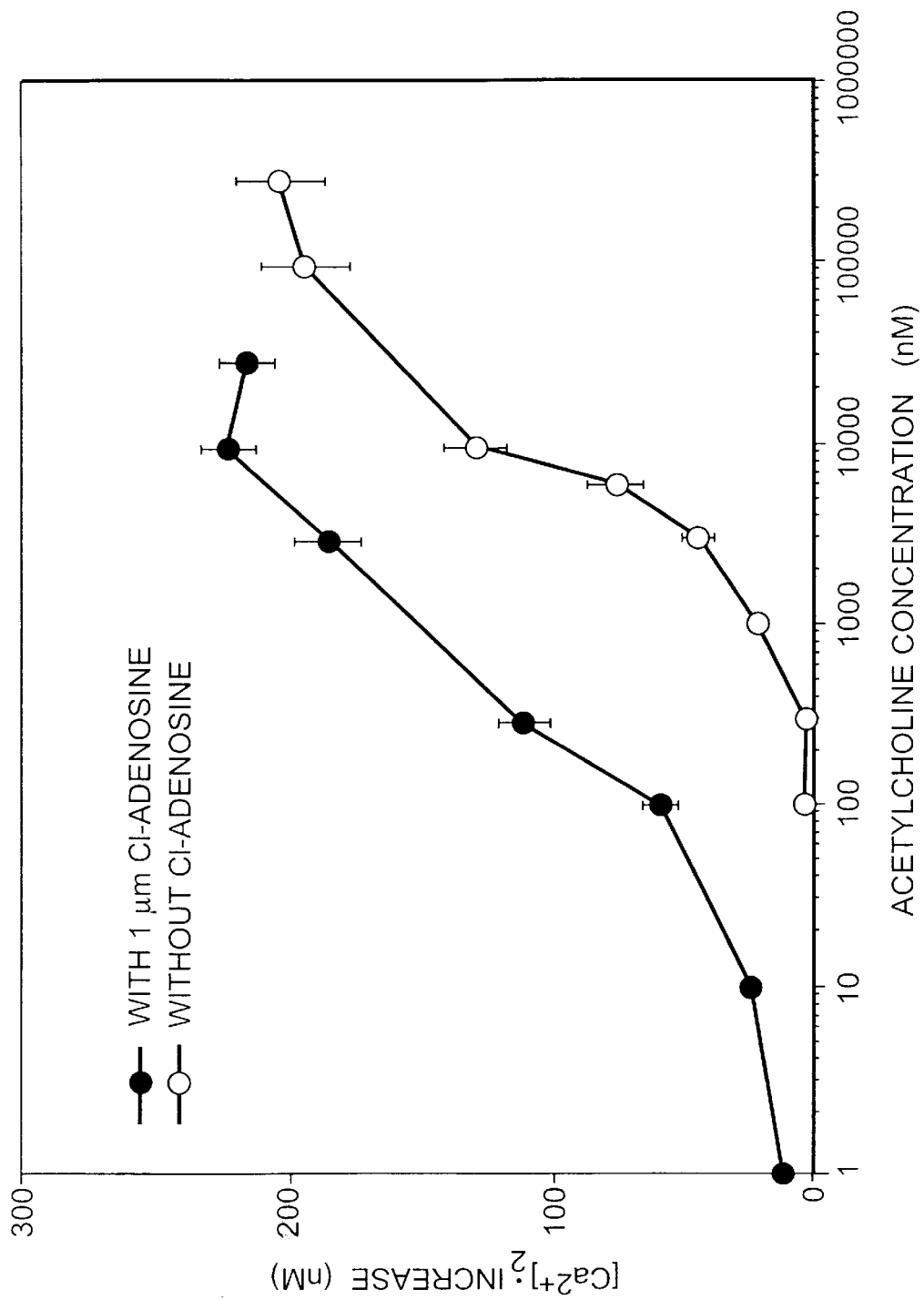
Figure 3:
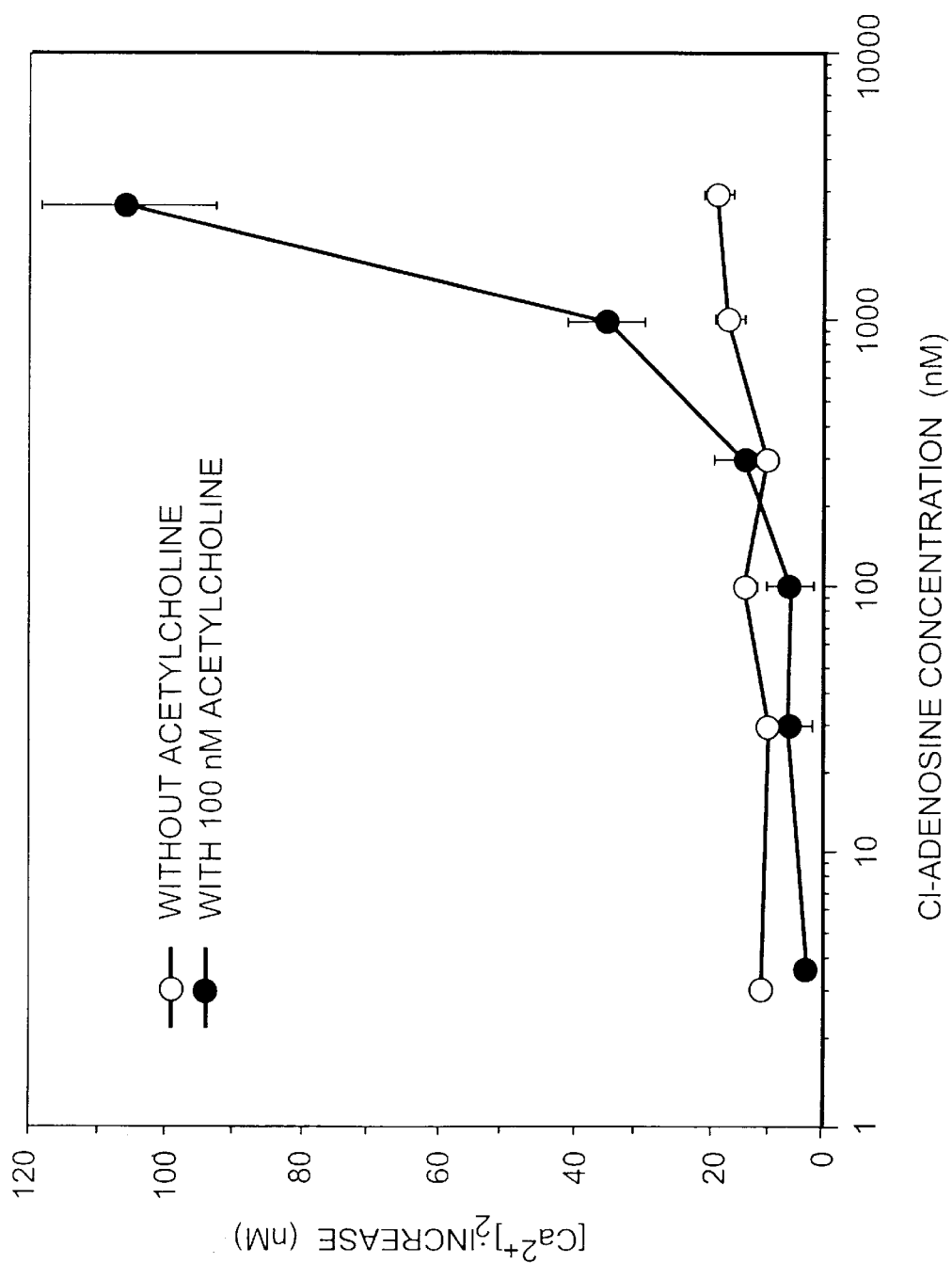

It has now been found that Cl-adenosine potentiates muscarinergic intracellular $Ca^{2+}$ release in cultured astrocytes of the rat in a concentration-dependent manner (see FIGS. 1 to 3; Tables 1 and 2). Thus even in the presence of 1 μM Cl-adenosine, an approximately thirty-fold potentiation of the intracellular $Ca^{2+}$ release induced by ACh is measured. This effect was not inhibitable by a nicotinic ACh receptor antagonist, but it was possible to block it by means of a muscarinic receptor antagonist (Table 3). Cl-Adenosine also potentiated the intracellular $Ca^{2+}$ release induced by the muscarinergic agonist oxotremorine-M (Table 4).

FIG. 1 shows the results of a fluorescence imaging experiment disclosed in the present application. 100 nM ACh and 1 μM Cl-adenosine applied alone are inactive. Their combination leads to a dramatic intracellular $Ca^{2+}$ increase within the cultured astrocytes. The same experiments carried out in $Ca^{2+}$-free medium show a lower, but still massive intracellular $Ca^{2+}$ increase within the cultured astrocytes when ACh and Cl-adenosine are applied together; this shows that intracellular $Ca^{2+}$ is mobilized.

FIG. 2 shows a fluorescence imaging experiment disclosed in the present application, wherein the dose-effect curve of the intracellular $Ca^{2+}$ increase induced by ACh in astrocytes is considerably shifted to the left on simultaneous action of 1 μM Cl-adenosine. The ACh level here only has to be 100 nM in order to produce an equally large $Ca^{2+}$ signal, for which a thirty-fold higher ACh concentration (more than 3 μM) would be necessary in the absence of a cooperating adenosine action.

FIG. 3 shows the results of a fluorescence imaging experiment disclosed in the present application, wherein the Cl-adenosine concentrations necessary for $Ca^{2+}$ mobilization in the presence of 100 nM Ach is determined.

A large part of the experiments demonstrating the potentiating Cl-adenosine effect (n>200) are carried out at an ACh concentration of 100 nM. At this low concentration, ACh is inactive on its own. Cl-adenosine on its own is also inactive over the concentration range tested (3 nM to 3 μM). Dose-effect experiments to determine the Cl-adenosine concentration necessary for the induction of a $Ca^{2+}$ signal in cooperation with 100 nM ACh show a potentiating effect at micromolar Cl-adenosine concentrations. The threshold concentration is 1 μM. Since Cl-adenosine corresponds to endogenous adenosine in its receptor affinity (Daly et al., *Life Sci.*, 28, pages 2083–2097, (1981)), this means that an increase in the extracellular adenosine level from the physiological nanomolar concentration range (Ballarin et al., *Acta Physiol. Scand.*, 142, pages 97–103, (1991)) to 1 μM is correspondingly also sufficient to bring into effect the sub-threshold ACh concentrations at the muscarinic receptor.

From these experimental results, it turns out that the adverse effect on cholinergic function mediated via muscarinic receptors in dementia can be improved by an increase in the extracellular adenosine concentration. The latter may be possible by coupled administration of an adenosine absorption inhibitor such as propentofylline (Parkinson et al., *Gem. Pharmacol.* 25, pages 1053–1058, (1994)). A pharmacological increase in the extracellular adenosine concentration would also allow a lower dose of the AChE inhibitor or muscarinic receptor agonists optionally used in a combination therapy, thereby decreasing the danger of undesired side effects.

The present invention relates to a combination preparation, comprising
   a) a compound which has an acetylcholinesterase-inhibitory action (so-called "AChE-inhibitor") or exhibits muscarinergic action;
   b) a compound which increases the endogenous extracellular adenosine level; and optionally
   c) a pharmaceutical excipient, said combination preparation having a super-additive increase in the muscarinic action in neurodegenerative disorders for simultaneous, separate or sequential administration. The term "super-additive" is understood to mean actions which are larger than the sum of the individual actions.

The invention further relates to a process for the production of the combination preparation, which comprises processing
   a) a compound which has an acetylcholinesterase inhibitory action or exhibits muscarinergic action;
   b) a compound which increases the endogenous extracellular adenosine level; and optionally
   c) a pharmaceutical excipient in a customary manner to give a pharmaceutical administration form.

Known compounds having AChE-inhibiting action are, for example, 9-amino-1,2,3,4-tetrahydroacridine (tacrine, COGNEX) and 1-benzyl-4-[(5,6-dimethoxy-1-indanon)-2-yl]methylpiperidine (E2020, ARICEPT). Known muscarinic agonists are, for example, milameline.

Compounds which increase the endogenous extracellular adenosine level are, for example, xanthine derivatives of the formula I

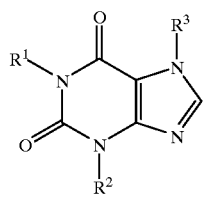

(I)

or a physiologically tolerable salt of the compounds of the formula I, where $R^1$ is
  a) an oxoalkyl group having 3 to 8 carbon atoms, whose carbon chain can be straight-chain or branched;
  b) a hydroxyalkyl group having 1 to 8 carbon atoms, whose carbon chain can be straight-chain or branched and whose hydroxyl group is a primary, secondary or tertiary alcohol function; or
  c) an alkyl group having 1 to 6 carbon atoms, whose carbon chain can be straight-chain or branched;
where $R^2$ is
  a) a hydrogen atom; or
  b) an alkyl group having 1 to 4 carbon atoms, whose carbon chain can be straight-chain or branched; and
where $R^3$ is
  a) a hydrogen atom;
  b) an alkyl group having 1 to 6 carbon atoms, whose carbon chain can be straight-chain or branched;
  c) an alkyl group having 1 to 6 carbon atoms, whose carbon chain is interrupted by an oxygen atom; or
  d) an oxoalkyl group having 3 to 8 carbon atoms, whose carbon chain can be straight-chain or branched.

Preferably, compounds of the formula I are used wherein
$R^1$ is an oxoalkyl group having 4 to 6 carbon atoms, whose carbon chain is straight-chain, or an alkyl group having 3 to 6 carbon atoms;
$R^2$ is an alkyl group having 1 to 4 carbon atoms; and
$R^3$ is an alkyl group having 1 to 4 carbon atoms or an oxoalkyl having 3 to 6 carbon atoms.

By way of example, the following compounds of the formula I are within the scope of the present invention:
  1-(5-oxohexyl)-3-methyl-7-n-propylxanthine (propentofylline),
  1-(5-hydroxy-5-methyl-hexyl)-3-methylxanthine,
  7-(ethoxymethyl-1-(5-hydroxy-5-methylhexyl)-3-methylxanthine,
  1-(5-oxohexyl)-3,7-dimethylxanthine,
  7-(2-oxopropyl)-1,3-di-n-butylxanthine, and
  1-hexyl-3,7-dimethylxanthine.

Most preferably, 1-(5-oxohexyl)-3-methyl-7-n-propylxanthine (propentofylline) is used as the compound according to formula I.

Accordingly, preferred combination preparations contain propentofylline and 1-benzyl-4-[(5,6-dimethoxy-1-indanon)-2-yl]methylpiperidine.

Suitable physiologically tolerable salts of the xanthine derivatives of the formula I are, for example, alkali metal, alkaline earth metal or ammonium salts, including those of physiologically tolerable organic ammonium bases.

The compounds of the formula I are prepared under standard conditions in a known manner. The processes for preparing the compounds according to formula I are described in U.S. Pat. Nos. 4,289,776; 4,833,146; and 3,737,433, which patents are incorporated herein in their entirety by specific reference. The starting substances of the reactions are known to those of one of ordinary skill in the art or can be easily prepared by methods known from the literature.

The combination preparation according to the present invention is suitable, for example, for the treatment of dementia, especially senile dementia.

The combination preparation according to the present invention can also include combination packs or compositions in which the constituents are placed side by side. The combination preparation according to the present invention can therefore be administered simultaneously, separately, or sequentially to human or animal body. The combination preparation according to the present invention can be employed as a dose unit in the form of pharmaceutical forms such as capsules (including microcapsules, which in general do not contain any pharmaceutical excipient), tablets (including coated tablets and pills) or suppositories. When using capsules, the capsule material can assume the function of the excipient and the contents can be present, for example, as a powder, gel, emulsion, dispersion or solution. It is particularly advantageous and simple, however, to prepare oral (peroral) formulations with the two active compound components a) and b) which contain the calculated amounts of the active compounds together with each desired pharmaceutical excipient. An appropriate suppository formulation for rectal therapy can also be used. Likewise, transdermal application in the form of ointments or creams, parenteral (intraperitoneal, subcutaneous, intravenous, intraarterial, or intramuscular) injection or infusion of solutions or oral administration of solutions which contain the combinations according to the invention is also possible.

Beside the active compounds, ointments, pastes, creams and powders can contain the customary excipients, e.g., animal and vegetable fats, waxes, paraffins, starch, tragacanth, cellulose derivatives, polyethylene glycols, silicones, bentonites, talc, zinc oxide, lactose, silicic acid, alumina, calcium silicate and polyamide powder, or mixtures of these substances.

The tablets, pills or granule bodies can be prepared by customary processes such as pressing, dipping or fluidized bed processes or pan coating and may contain excipients and other customary auxiliaries such as gelatin, agarose, starch (e.g., potato, corn or wheat starch), celluloses such as ethylcellulose, silica, various sugars such as lactose, magnesium carbonate and/or calcium phosphates. The coating solution usually consists of sugar and/or starch syrup and mostly additionally contains gelatin, gum arabic, polyvinylpyrrolidone, synthetic cellulose esters, surface-active substances, plasticizers, pigments and similar additives corresponding to the prior art. For the production of the pharmaceutical forms, any customary flow-regulating agent, lubricant or glidant such as magnesium stearate and release agents can be used.

The preparations preferably have the form of coating/core tablets or multilayer tablets, the active component b) being in the coating or in the core of one layer, while the active component a) is in the core or in the coating or in another layer. The active compound components can also be prepared in delayed-release form or adsorbed on release-delaying material or included in the release-delaying material (e.g., those based on cellulose such as hydroxyethylcellulose, or polystyrene resin. Delayed release of the active compounds can also be achieved by providing the layer or the compartment concerned with customary enteric coatings.

The dose to be used is, of course, dependent on various factors such as the living being to be treated (i.e., human or animal), age, weight, general state of health, the degree of severity of the symptoms, the disorder to be treated, possible concomitant disorders (if present), the nature of the concomitant treatment with other pharmaceuticals, or the frequency of the treatment. The doses are in general administered several times per day and preferably one to three times per day. The amounts of individual active compounds used are based on the recommended daily dose of the respective individual active compound and, in the combination preparation, should in general be from 10% to 100% of the recommended daily dose. This amount is preferably from 20% to 80%, and most preferably 50% of the recommended daily dose.

Suitable therapy with the combination preparation according to the present invention thus comprises, for example, the administration of an individual dose comprised of 1) from about 100 mg to about 600 mg, preferably from about 200 mg to about 400 mg, and most preferably about 300 mg of propentofylline, and
2) from about 2 mg to about 20 mg, preferably from about 5 mg to about 10 mg, of 1-benzyl-4-[(5,6-dimethoxy-1-indanon)-2-yl]methylpiperidine, to a patient is need of said therapy, where the amount is dependent, of course, on the number of individual doses and the illness to be treated. An individual dose can consist of several, simultaneously administered dose units.

The following examples are illustrative of the invention embodied herein without being limiting in nature.

ASTROCYTE CULTURES

The cortex astrocyte cultures originate from the cerebral cortex of 19–20 day-old Wistar rat embryos which were taken from the dam after sacrifice under ether anesthesia. After preparation of the brain, cortical tissue was aspirated with a pipette and taken up in Dulbecco's modified Eagle medium ("DMEM") with addition of 15% fetal calf serum. After filtering through lens tissue, the cell suspension was transplanted to glass slides (coated with polyethylenimine) and cultured in culture bottles under standard conditions in an incubator with change of medium twice per week. After approximately 7 days, the cells were harvested and, after trypsinization (in order to eliminate nerve cells) transplanted again at a concentration of $5 \times 10^4$ cells/cm$^2$ and cultured for a further 6–8 days until the start of the experiment. These cultures consisted to more than 95% of astrocytes which had a positive immune reaction for the astrocyte label GFAP (acidic glia fibrillar protein).

Fluorescence Imaging Experiments for Measurement of the Intracellular Ca$^{2+}$ Concentration and Experimental Influencing Thereof At the start of the experiment (6–8 days after retransplantation), the cultured astrocytes were loaded with a Ca$^{2+}$ fluorescent label, to be specific by incubation with 5 $\mu$M fura-2-acetoxymethyl ester (Molecular Probes) in BHKR (bicarbonated, HEPES-buffered Krebs-Ringer solution) at 37° C. for 1 hour. After the loading, the glass slides containing the cultured astrocytes were transferred into a measuring chamber and installed on the inverted fluorescence microscope (Zeiss Axiovert 100, Zeiss Fluar 40× objective) belonging to the fluorescence imaging measuring station. Here the chamber was continuously perfused with temperature-controlled (37° C.) BHKR at a flow rate of 600 ml/min during the experimental period (as a rule 20–30 min).

Measurement was carried out using the FUCAL fluorescence imaging system (T.I.L.L. Photonics GmbH, Planegg), and after excitation by two excitation wavelengths at 340 and 380 nm the emitted fluorescence above the wavelength of 420 nm was measured with the aid of a CCD camera (CS 90, Theta System, Gröbenzell) and the corresponding Ca$^{2+}$ concentration was calculated. The measurements were carried out at time intervals of 12 seconds in each case before, during and after addition of the various test substances to the perfused medium. Changes in the intracellular Ca$^{2+}$ concentration were determined at the individual cell level, to be specific in various, in each case adequately defined, measuring windows.

The various test substances (acetylcholine or oxotremorine in the presence or absence of Cl-adenosine) were as a rule added to the perfusion medium for the period of 1 minute. Since the induced intracellular Ca$^{2+}$ rises were transient, the changes in the intracellular Ca$^{2+}$ concentrations shown in the result tables and curves were based on the peak values measured in each case.

The increase in the intracellular Ca$^{2+}$ concentration (nM) is represented in Table 1.

TABLE 1

| Acetylcholine | intracellular Ca$^{2+}$ concentration [nM] | |
|---|---|---|
| (nM) | without addition | +1 $\mu$M Cl-adenosine |
| 3 |  | 14.17 ± 2.87 |
| 10 |  | 23.59 ± 4.25 |
| 100 | 2.18 ± 1.8 | 56.27 ± 6.7 |
| 300 | 1.4 ± 1.57 | 107.27 ± 9.41 |
| 1000 | 19.83 ± 3.24 |  |
| 3000 | 41.91 ± 5.59 | 182.18 ± 12.27 |
| 6000 | 73.79 ± 10.94 |  |
| 10000 | 126.79 ± 12.07 | 220.99 ± 10.97 |
| 30000 |  | 214.20 ± 10.38 |
| 100000 | 192.74 ± 16.61 |  |
| 300000 | 203.49 ± 15.46 |  |

Table 1 contains mean values±SEM, wherein the number of measured cells was 45 (n=45) for each measurement. Table 1 shows that the dose-effect curve of the intracellular Ca$^{2+}$ increase induced by ACh in astrocytes is considerably shifted to the left on simultaneous action of 1 $\mu$M Cl-adenosine. The ACh level only has to be 100 nM here in order to produce an equally large Ca$^{2+}$ signal, for which a thirty-fold higher ACh concentration (more than 3 $\mu$M) would be necessary in the absence of a cooperating adenosine action. The critical adenosine increase needed for this cooperative effect is in a range which should be achieved pharmacologically by therapy with the adenosine absorption blocker propentofylline.

TABLE 2

| Cl-adenosine | intracellular Ca$^{2+}$ concentration [nM] | |
|---|---|---|
| (nM) | without addition | +100 nM acetylcholine |
| 3 | 10.54 ± 1.57 | 1.57 ± 2 |
| 30 | 8.29 ± 1.69 | 5.06 ± 3.28 |
| 100 | 11.31 ± 1.92 | 4.82 ± 3.43 |
| 300 | 8.45 ± 1.64 | 11.56 ± 4.42 |
| 1000 | 14.2 ± 2.23 | 32.35 ± 5.49 |
| 3000 | 15.99 ± 2.26 | 104.16 ± 13.82 |

Table 2 contains mean values±SEM, wherein the number of measured cells was 40 (n=40) for each measurement. Table 2 shows Cl-adenosine concentrations necessary for Ca$^{2+}$ mobilization in the presence of 100 nM ACh.

The effect of antagonists on the nicotinic acetylcholine receptor (i.e., hexamethonium) and the muscarinic acetylcholine receptor (i.e., pFHHSiD) on the increase in the intracellular $Ca^{2+}$ concentration by 100 nM acetylcholine and 1 μM Cl-adenosine in cultured cortex astrocytes is represented in Table 3.

TABLE 3

| Test substance | $Ca^{2+}$ increase | [% of the control] |
|---|---|---|
| 10 μM hexamethonium | 90.7 ± 6.26 | n = 13 |
| 50 nM pFHHSiD[1] | 53.9 ± 7.2 | n = 19 |
| 200 nM pFHHDSiD[1] | 22 ± 4.7 | n = 5 |

[1]pFHHSID (hexahydrosiladifenidol hydrochloride, p-fluoro analog); manufacturer: RBI (Research Biochemicals International).

Table 3 contains mean values±SEM in percent of the intracellular $Ca^{2+}$ increase which was achieved in the absence of the antagonists by 100 nM acetylcholine and 1 μM Cl-adenosine (control value=100%). As control value, an intracellular $Ca^{2+}$ increase of 98.4±6.4 nM was measured (n=125). Table 3 shows that the ACh effect potentiated by Cl-adenosine is a representative ACh effect mediated via muscarinic receptors, which is antagonized by a muscarinic receptor blocker, but not by a nicotinic receptor blocker.

Table 4 below, shows the effect of Cl-adenosine and the muscarinic acetylcholine receptor agonists oxotremorine-M on the intracellular $Ca^{2+}$ content in cultured cortex astrocytes.

TABLE 4

| Acetylcholine receptor agonist | $Ca^{2+}$ increase [nM] |
|---|---|
| 100 nM oxotremorine-M | 3.3 ± 5.7 |
| 100 nM oxotremorine +1 μM Cl-adenosine | 93.3 ± 23.7 |

Table 4 contains mean values±SEM, wherein the number of measured cells was 6 (n=6) for each measurement. Table 4 shows that Cl-adenosine also potentiates the $Ca^{2+}$ signal induced by a muscarinic receptor agonist.

What is claimed:

1. A composition comprising
   a) a compound which has an acetylcholinesterase-inhibitory action or acts as a muscarinic receptor agonist; and
   b) a compound which increases the endogenous extracellular adenosine level;
wherein the composition has a super-additive increase in muscarinic agonism in neurodegenerative disorders.

2. A composition according to claim 1, wherein the compound which has an acetylcholinesterase-inhibitory action is 9-amino-1,2,3,4-tetrahydroacridine, 1-benzyl-4-[(5,6-dimethoxy-1-indanon)-2-yl]methylpiperidine, or milameline.

3. A composition according to claim 1, wherein the compound which has an acetylcholinesterase-inhibitory action is 1-benzyl-4-[(5,6-dimethoxy-1-indanon)-2-yl] methylpiperidine.

4. A composition according to claim 1, wherein the compound which increases the endogenous extracellular adenosine level is a xanthine derivative according to formula I

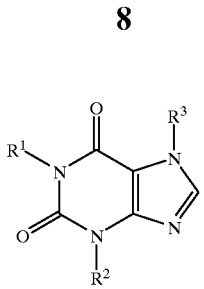

or a physiologically tolerable salt of the compounds according to formula I, where $R^1$ is
   a) an oxoalkyl group having 3 to 8 carbon atoms, whose carbon chain is straight-chain or branched;
   b) a hydroxyalkyl group having 1 to 8 carbon atoms, whose carbon chain is straight-chain or branched and whose hydroxyl group is a primary, secondary, or tertiary alcohol functional group; or
   c) an alkyl group having 1 to 6 carbon atoms, whose carbon chain is straight-chain or branched;
where $R^2$ is
   a) a hydrogen atom; or
   b) an alkyl group having 1 to 4 carbon atoms, whose carbon chain is straight-chain or branched; and
where $R^3$ is
   a) a hydrogen atom;
   b) an alkyl group having 1 to 6 carbon atoms, whose carbon chain is straight-chain or branched;
   c) an alkyl group having 1 to 6 carbon atoms, whose carbon chain is interrupted by an oxygen atom; or
   d) an oxoalkyl group having 3 to 8 carbon atoms, whose carbon chain is straight-chain or branched.

5. A composition according to claim 4, wherein
$R^1$ is an oxoalkyl group having 4 to 6 carbon atoms, whose carbon chain is straight-chain, or an alkyl group having 3 to 6 carbon atoms;
$R^2$ is an alkyl group having 1 to 4 carbon atoms; and
$R^3$ is an alkyl group having 1 to 4 carbon atoms or an oxoalkyl having 3 to 6 carbon atoms.

6. A composition according to claim 1, wherein the compound which increases the endogenous extracellular adenosine level is
   1-(5-oxohexyl)-3-methyl-7-n-propylxanthine,
   1-(5-hydroxy-5-methyl-hexyl)-3-methylxanthine,
   7-(ethoxymethyl-1-(5-hydroxy-5-methylhexyl)-3-methylxanthine,
   1-(5-oxohexyl)-3,7-dimethylxanthine,
   7-(2-oxopropyl)-1,3-di-n-butylxanthine, or
   1-hexyl-3,7-dimethylxanthine.

7. A composition according to claim 1, wherein the compound which increases the endogenous extracellular adenosine level is 1-(5-oxohexyl)-3-methyl-7-n-propylxanthine.

8. A composition according to claim 1, wherein
   a) the compound which has an acetylcholinesterase-inhibitory action is 1-benzyl-4-[(5,6-dimethoxy-1-indanon)-2-yl]methylpiperidine, and
   b) the compound which increases the endogenous extracellular adenosine level is 1-(5-oxohexyl)-3-methyl-7-n-propylxanthine.

9. A composition according to claim 1, comprising
   a) about 100 mg to about 600 mg of the compound which has an acetylcholinesterase-inhibitory action or exhibits muscarinergic action; and b) about 2 mg to about 20 mg of the compound which increases the endogenous extracellular adenosine level.

10. A composition according to claim 9, comprising about 200 mg to about 400 mg of the compound which has an acetylcholinesterase-inhibitory action or acts as a muscarinic receptor agonist.

11. A composition according to claim 10, comprising about 200 mg to about 300 mg of the compound which has an acetylcholinesterase-inhibitory action or acts as a muscarinic receptor agonist.

12. A composition according to claim 9, comprising about 5 mg to about 10 mg of the compound which increases the endogenous extracellular adenosine level.

13. A composition according to claim 1, comprising
   a) about 2 mg to about 20 mg 1-benzyl-4-[(5,6-dimethoxy-1-indanon)-2-yl]methylpiperidine; and
   b) about 100 mg to about 600 mg 1-(5-oxohexyl)-3-methyl-7-n-propylxanthine.

14. A composition according to claim 13, comprising about 200 mg to about 400 mg 1-(5-oxohexyl)-3-methyl-7-n-propylxanthine.

15. A composition according to claim 14, comprising about 200 mg to about 300 mg 1-(5-oxohexyl)-3-methyl-7-n-propylxanthine.

16. A composition according to claim 13, comprising about 5 mg to about 10 mg 1-benzyl-4-[(5,6-dimethoxy-1-indanon)-2-yl]methylpiperidine.

17. A composition according to claim 1, comprising
   a) about 5 mg to about 10 mg 1-benzyl-4-[(5,6-dimethoxy-1-indanon)-2-yl]methylpiperidine, and
   b) about 100 mg to about 300 mg 1-(5-oxohexyl)-3-methyl-7-n-propylxanthine.

18. A composition according to claim 1, wherein the composition further comprises a pharmaceutical excipient.

19. A method for the treatment of neurodegenerative disorders, comprising administering to a patient in need of said treatment an amount effective therefor of the composition comprising a compound which has an acetylcholinesterase-inhibitory action or acts as a muscarinic receptor agonist and a compound which increases the endogenous extracellular adenosine level.

20. The method according to claim 19, wherein said neurodegenerative disorder is senile dementia.

21. The method according to claim 19, wherein the compound which has an acetylcholinesterase-inhibitory action or acts as a muscarinic receptor agonist and the compound which increases the endogenous extracellular adenosine level are administered simultaneously to the patient.

* * * * *

UNITED STATES PATENT AND TRADEMARK OFFICE
CERTIFICATE OF CORRECTION

PATENT NO. : 6,037,347
DATED : March 14, 2000
INVENTOR(S) : Schubert et al.

It is certified that error appears in the above-identified patent and that said Letters Patent is hereby corrected as shown below:

Column 3,
Line 51, reads "7-(ethoxymethyl-1-(5-hydroxy-5-methylhexyl)-3-" and should read as -- 7-(ethoxymethyl)-1-(5-hydroxy-5-methylhexyl)-3- --.

Column 4,
Line 5, reads "tions are known to those of one of ordinary skill in the art" and should read as -- tions are known to those of ordinary skill in the art --.
Line 16, reads "sequentially to human or animal body. The combination" and should read as -- sequentially to a human or animal body. The combination --.
Line 66, reads " hydroxyethylcellulose, or polystyrene resin. Delayed release" and should read as -- hydroxyethylcellulose, or polystyrene resin). Delayed release --.

Column 7,
Line 28, reads "muscarinic acetylcholine receptor agonists oxotremorine-M" and should read as -- muscarinic acetylcholine receptor agonist oxotremorine-M --.
Line 37, reads "100 nM oxotremorine    93.3±23.7" and should read as
-- 100 nM oxotremorine-M     93.3±23.7 --.

Column 8,
Line 47, reads as ""7-(ethoxymethyl-1-(5-hydroxy-5-methylhexyl)-3-" and should read as -- 7-(ethoxymethyl)-1-(5-hydroxy-5-methylhexyl)-3- --.

Signed and Sealed this

Seventeenth Day of September, 2002

Attest:

Attesting Officer

JAMES E. ROGAN
*Director of the United States Patent and Trademark Office*